United States Patent
Hirschel et al.

(10) Patent No.: US 8,679,071 B2
(45) Date of Patent: Mar. 25, 2014

(54) INJECTION DEVICE COMPRISING A MECHANICAL LOCK

(75) Inventors: Juerg Hirschel, Aarau (CH); Ulrich Moser, Heimiswil (CH); Christian Schrul, Burgdorf (CH); Markus Tschirren, Kirchberg (CH)

(73) Assignee: TecPharma Licensing AG, Burgdorf (CH)

( * ) Notice: Subject to any disclaimer, the term of this patent is extended or adjusted under 35 U.S.C. 154(b) by 725 days.

(21) Appl. No.: 12/371,350

(22) Filed: Feb. 13, 2009

(65) Prior Publication Data
US 2009/0227955 A1 Sep. 10, 2009

Related U.S. Application Data

(63) Continuation of application No. PCT/CH2007/000389, filed on Aug. 10, 2007.

(30) Foreign Application Priority Data

Aug. 14, 2006 (DE) .......................... 10 2006 038 123

(51) Int. Cl.
*A61M 5/00* (2006.01)
(52) U.S. Cl.
USPC ............ 604/232; 604/234; 604/181; 604/207
(58) Field of Classification Search
USPC .......... 604/207–211, 232, 234, 310, 181, 187
See application file for complete search history.

(56) References Cited

U.S. PATENT DOCUMENTS

| | | | |
|---|---|---|---|
| 3,353,718 A | | 11/1967 | McLay |
| 5,092,842 A | * | 3/1992 | Bechtold et al. .............. 604/135 |
| 5,112,317 A | | 5/1992 | Michel |
| 5,378,233 A | * | 1/1995 | Haber et al. .................... 604/83 |
| 5,383,865 A | * | 1/1995 | Michel ......................... 604/232 |
| 5,647,856 A | | 7/1997 | Eykmann et al. |
| 6,004,298 A | * | 12/1999 | Levander ...................... 604/211 |
| 6,048,336 A | | 4/2000 | Gabriel |
| 6,793,646 B1 | | 9/2004 | Giambattista et al. |
| 2004/0186431 A1 | | 9/2004 | Graf et al. |
| 2004/0186443 A1 | | 9/2004 | Covino et al. |
| 2005/0065477 A1 | * | 3/2005 | Jost .............................. 604/207 |
| 2005/0137571 A1 | * | 6/2005 | Hommann ................... 604/500 |
| 2005/0154351 A1 | | 7/2005 | Graf et al. |
| 2005/0222540 A1 | | 10/2005 | Kirchhofer |
| 2005/0261634 A1 | | 11/2005 | Karlsson |

FOREIGN PATENT DOCUMENTS

| | | |
|---|---|---|
| DE | 0 635 934 | 10/1936 |
| DE | 198 21 934 C1 | 11/1999 |
| DE | 697 21 700 | 3/2004 |
| DE | 699 22 027 | 10/2005 |

(Continued)

*Primary Examiner* — Bhisma Mehta
*Assistant Examiner* — Bradley G Thomas, Jr.
(74) *Attorney, Agent, or Firm* — Dorsey & Whitney LLP; David E. Bruhn, Esq.

(57) ABSTRACT

An injection device with a housing and an operating element or coupling element mounted in the housing in such a way that the operating element or coupling element may be retained in a first position by a first holding connection and may be displaced into a second position that is axially offset relative to the first position after introducing an ampoule. In some embodiments, the operating element or coupling element may be retained by a second holding connection in the second position.

8 Claims, 12 Drawing Sheets

(56) References Cited

FOREIGN PATENT DOCUMENTS

| DE | 10 2004 055 298 A1 | 5/2006 |
|----|---|---|
| DE | 603 02 335 | 8/2006 |
| EP | 0 554 995 A1 | 8/1993 |
| EP | 0 937 471 | 8/1999 |
| WO | WO 00/41752 | 7/2000 |
| WO | 00/62839 A2 | 10/2000 |
| WO | 01/72361 A1 | 10/2001 |
| WO | 02/092153 A2 | 11/2002 |
| WO | 03/000317 A1 | 1/2003 |
| WO | WO 03/053499 | 7/2003 |
| WO | WO 2004/006997 | 1/2004 |
| WO | WO 2005/072796 | 8/2005 |
| WO | 2007/082400 A1 | 7/2007 |

\* cited by examiner

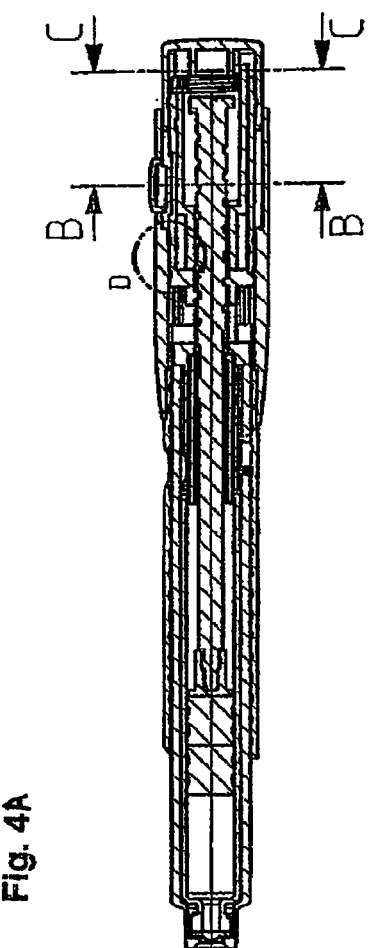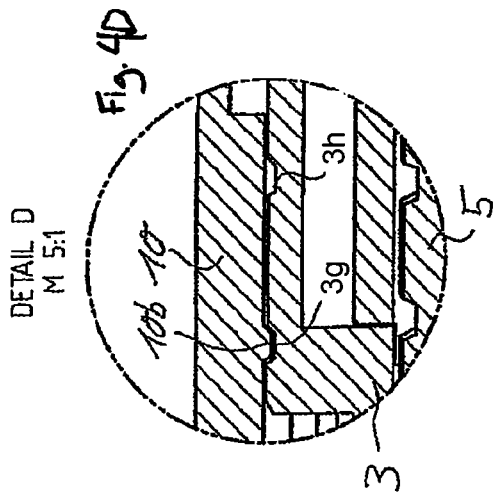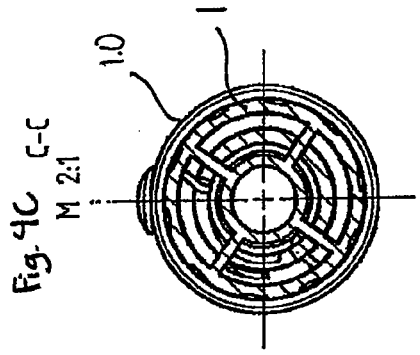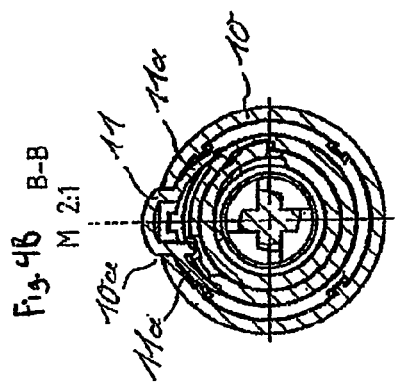

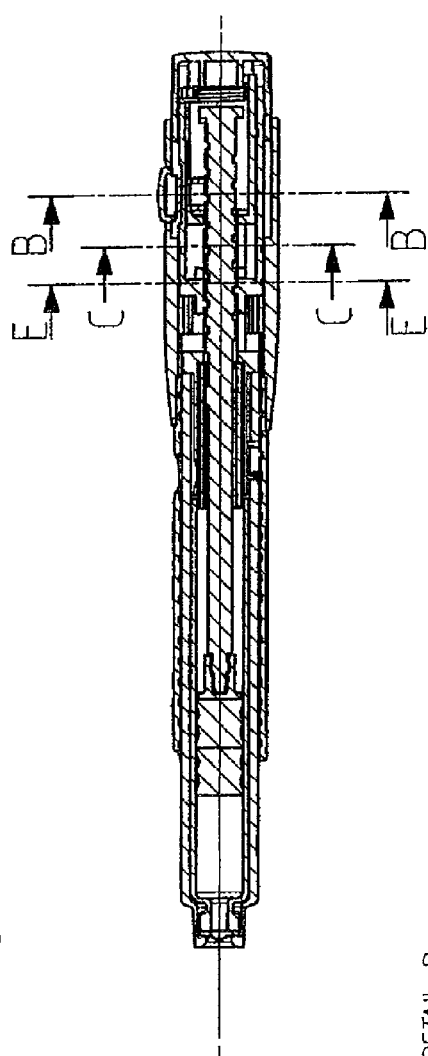
Fig. 5A
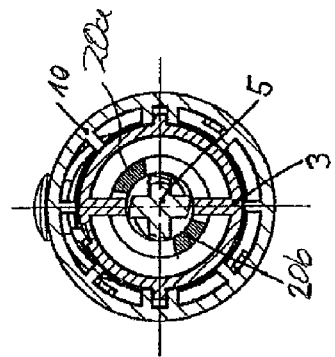
Fig. 5E E-E
M 2:1
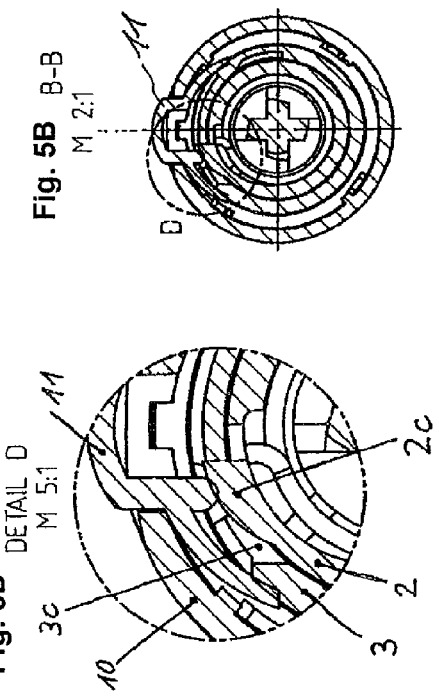
Fig. 5C C-C
M 2:1
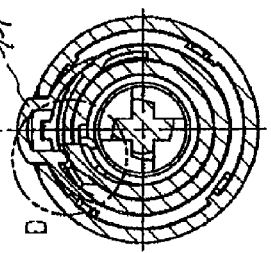
Fig. 5B B-B
M 2:1
Fig. 5D DETAIL D
M 5:1

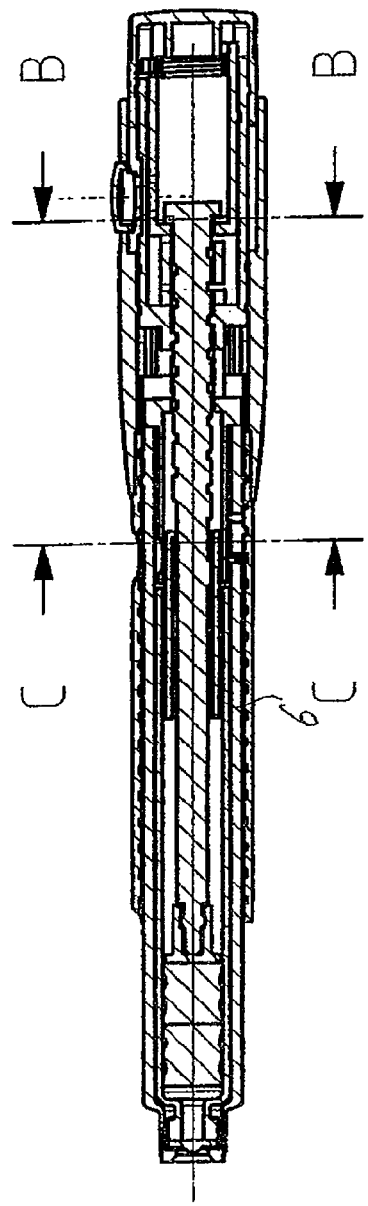
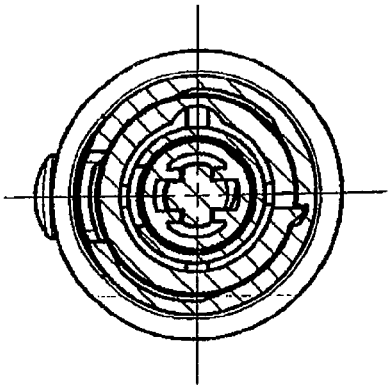
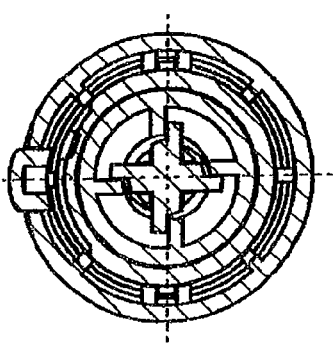
Fig. 6A
Fig. 6B B-B M 2:1
Fig. 6C C-C M 2:1

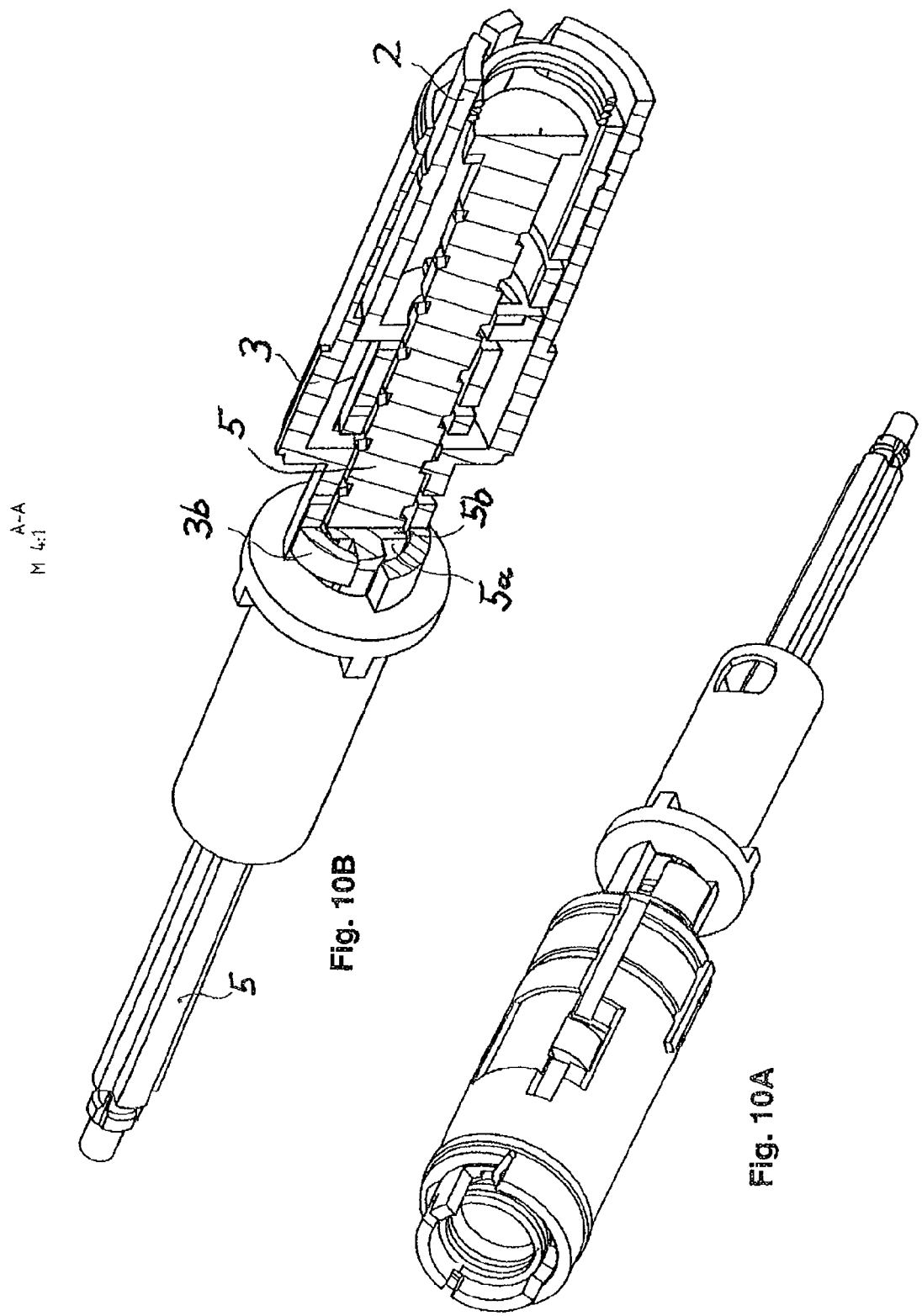

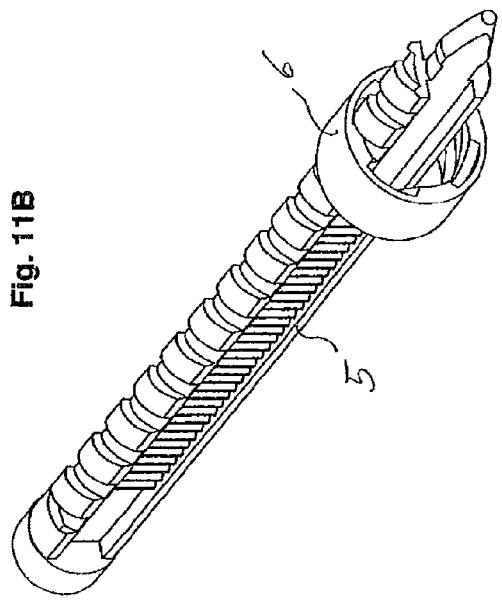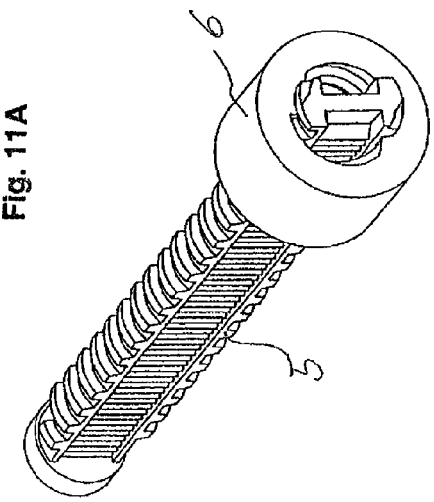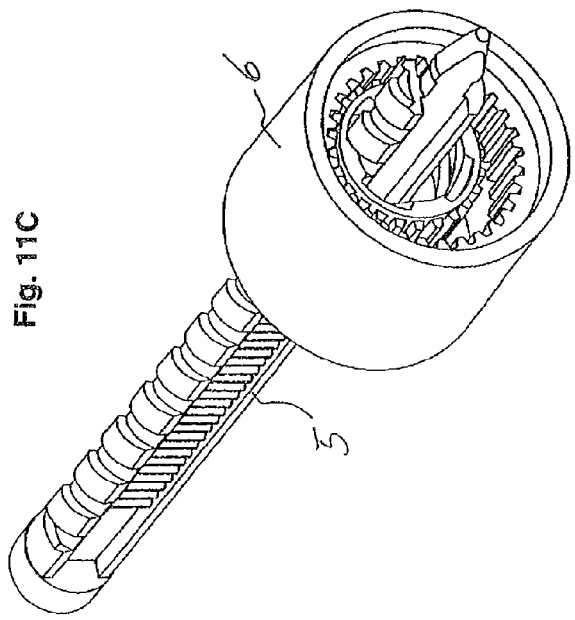

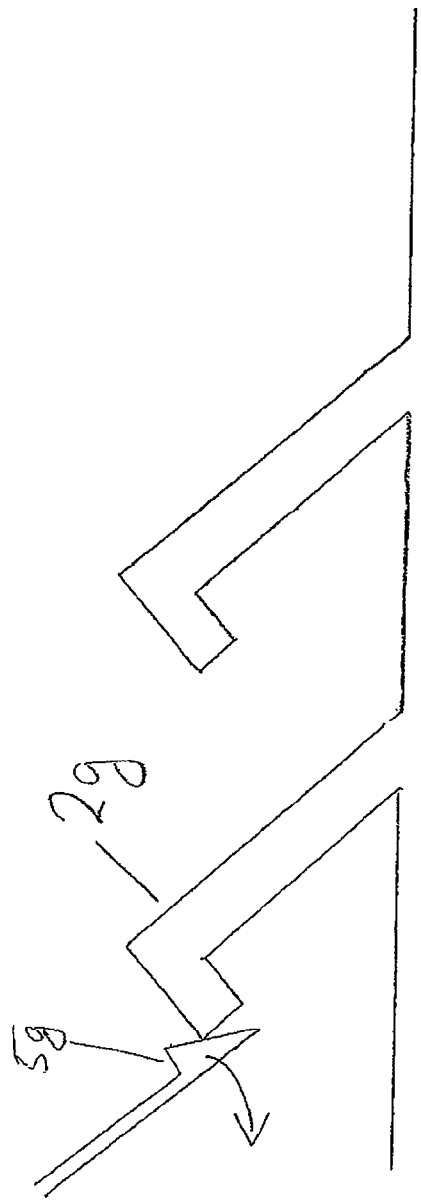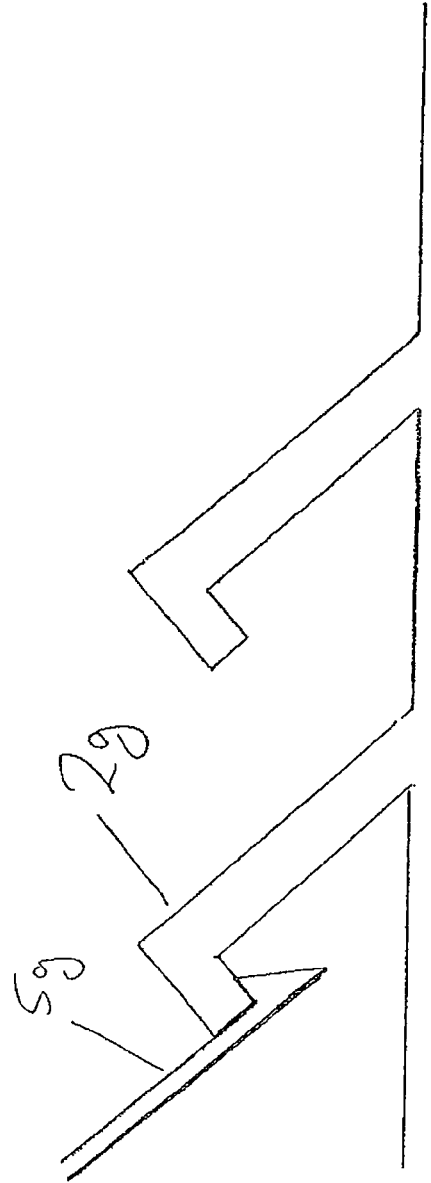

INJECTION DEVICE COMPRISING A MECHANICAL LOCK

CROSS-REFERENCED RELATED APPLICATIONS

This application is a continuation of International Patent Application No. PCT/CH2007/000389 filed Aug. 10, 2007, which claims priority to German Patent Application No. DE 10 2006 038 123.8 filed Aug. 14, 2006, the contents of all of which are incorporated in their entirety herein by reference.

FIELD OF THE INVENTION

The present invention relates to devices for delivering, injecting, infusing, dispensing or administering a substance, and to methods of making and using such devices. More particularly, it relates to embodiments of a threaded rod for an injection device or an injection pen, as well as a real-time display for displaying the quantity of a dispensable substance contained in the injection device or for displaying the substance already dispensed from the injection device, a mechanical lock used prior to mixing an ampoule (e.g., a two-chamber ampoule), a threaded guide for different pitches of the plunger rod, a claw lock, and to an injection device with such a threaded rod and/or with such a real-time display and/or a mechanical lock and/or a threaded guide and/or a claw lock.

BACKGROUND

To set the quantity of a substance to be dispensed from an injection device, at least one dose setting knob or a dose setting ring usually effects a setting movement on a setting element. For example, by rotating the dose setting element, and the degree of rotation, e.g., the angle of rotation, the quantity of substance to be dispensed from the injection device during the next injection procedure is defined. In the case of an injection device designed to dispense a fixed, pre-set quantity of substance, e.g., a fixed-dose pen, the setting movement is effected in order to prime the pen in readiness for dispensing a pre-defined dose.

SUMMARY

Embodiments provide a threaded rod and an injection device that permits a robust, durable and simple setting procedure for a fixedly set dose (fixed dose).

In one embodiment, the present invention comprises an injection device with a housing and an operating element or coupling element mounted in the housing in such a way that the operating element or coupling element may be retained in a first position by a first holding connection and may be displaced into a second position that is axially offset relative to the first position after introducing an ampoule. In some embodiments, the operating element or coupling element may be retained by a second holding connection in the second position.

According to some embodiments, the threaded rod of the injection device is configured such that it assumes a pre-defined, fixed position of rotation in co-operation with one or more locating elements disposed on the pen or the housing of the pen or also coupled with the setting element. For example, elastic snapper elements or catch elements biased radially inwardly or radially outwardly may locate in locating or positioning regions of the threaded rod to establish a coupling between the threaded rod and the pen or between the threaded rod and a setting element. The threaded rod may include locating or positioning regions, grooves or ridges in the longitudinal direction of the threaded rod, and may interrupt the thread on the external face of the threaded rod in a manner that provides the threaded rod with a cross-sectional shape in the form of a star with three, four, five, six or more tines or webs, which may facilitate permitting a robust and simple setting of a fixedly, pre-defined dose (fixed dose). That is, for a threaded rod with a cruciform cross-sectional shape with four tines, the rod may be rotated so that it can assume four defined and stable positions of rotation. In the stable positions of rotation, one or more locating elements, which are disposed around and correspond to the specific shape of the threaded rod, for example, locate or position in the grooves of the threaded rod and hold it in four defined positions of rotation in the case of a star-shaped design. A rotation of the threaded rod may thus lead to stable and defined positions of rotation of the threaded rod after 90°, 180°, 270° and another multiple of 90°, for example.

The threaded rod may be configured such that at least in the region of the grooves or axially extending locating regions, the outer or peripheral regions of the threaded rod have a slight incline, so that the locating elements, which may be radially biased in the direction towards the threaded rod and which permit a rotation of the threaded rod in one direction due to a sliding action across the inclined regions and establish a lock by means of a rotation in the locking or opposite direction by locating in the locating regions, can be released from or moved out of the engaged position and forced out of the locating regions when the threaded rod is rotated opposite the locking direction so that they are guided by the rotating movement across the inclined outer regions into the adjacent locating region. Due to an inclined design of the outer regions, a tine or web of the threaded rod includes an upper and a lower flank between two grooves or locating regions. The upper flank may be disposed on the side from which the locating element is no longer intended to be released in order to move across the outer region, thereby enabling the threaded rod to be blocked by the locating element so that it can no longer rotate. The lower or relatively smaller flank, may be configured to ease rotation of the threaded rod and movement of the locating element. A relatively smaller flank means the locating element need only to be pushed out along the distance of the smaller flank to the inclined region to enable the threaded rod to rotate. The locating elements may be provided with an incline, which may be designed so that it matches the incline of the peripheral region of the threaded rod, for example, and which facilitates or permits a releasing movement of the locating element in a releasing direction during a rotating movement.

The threaded rod may include a wider region at its proximal end, such as a circumferentially extending ring or radially projecting web from which at least one locating element, e.g., one or more webs, projects out in the distal direction in order to establish a claw lock with co-operating mating elements when the threaded rod has been fully pushed in for example, and the threaded rod locates in co-operating mating elements or claws so that any further rotating movement of the threaded rod or dose setting element relative to the injection device is blocked and the injection device can therefore no longer be used.

In another embodiment, an injection device includes a threaded rod of the types described above.

A dose setting element, such as a dose setting knob or a rotating knob provided on the injection device, may be coupled to other elements, such as a rotating sleeve or a rotating element. The dose to be dispensed (e.g., a priming dose or a delivery dose) may be set by means of the dose setting element. A spring element, such as a tension spring, associated with the dose setting element may be tensed by rotation of the dose setting element, and may store energy for the subsequent injection and forward movement of the threaded rod and/or triggering element release, when operated. A rotating sleeve coupled to the dose setting element, or the dose setting element itself, may include at least one, two or more inwardly biased locating elements, which when two or another even number of locating elements are provided, lie opposite one another. The locating elements are configured to locate in matching locating regions of the threaded rod and permit a rotation of the threaded rod in one direction relative to the rotating sleeve or to the dose setting element. When the rotating sleeve or the dose setting element is rotated in the opposite direction, the locating elements remain located with the threaded rod and drive it with them so that the energy stored in the torsion spring due to the setting movement can be converted into a rotating movement of the threaded rod.

At least one locating element biased radially outwardly may also be provided on the rotating sleeve or the dose setting element, which may be configured to locate in a window or a groove or recess of the injection device for example, so that the rotating sleeve or dose setting element can be retained or locked in a pre-defined position of rotation after setting the dose or priming the injection device, for example. The retaining element used to establish the lock may be released again by means of a release button, for example, and when the release button is operated, the locating element biased radially outwardly is pushed in a direction directed radially inwardly again for example, so that the rotating sleeve or dose setting element is no longer coupled with the injection device and a rotating movement is made possible by the torsion spring, for example.

The injection device may be configured with at least one guide element, either integrated as part of the injection device and fixedly connected to the injection device or provided as a separate element, which includes at least one elastic retaining element biased radially inwardly and configured to locate in at least one locating region of the threaded rod to enable a rotating movement of the threaded rod relative to the injection device in one direction, and to lock it in the opposite direction. The guide element may also be configured with an internal thread, which may comprise one or more partial-thread segments. This internal thread or the partial-thread segments may be configured with several contact faces (see e.g., the thread of FIG. 9), thereby permitting a thread engagement for threads of different pitches. For example, the thread segments may be designed so that different threaded rods with an external thread of a different pitch may be reliably guided between a minimum pitch defined by first contact faces of the internal thread and a maximum pitch defined by second contact faces of the internal thread. This enables different doses to be set by the same rotating movement depending on the substance to be administered due to the fact that threaded rods with external threads of differing pitches can be used.

The injection device may be configured with locating elements or claws for establishing a claw coupling with co-operating locating elements or claws of the threaded rod. The locating elements of the injection device may be disposed on a surface of a rotating sleeve, a guide sleeve or the injection device itself pointing in the proximal direction.

Embodiments further relate to an injection device with a transmission element, which is coupled with a dispensing element of the injection device, such as a plunger rod or threaded rod for example, which can be coupled with an indicator element which can be coupled with an ampoule which can be introduced into the injection device.

When a display is provided on an injection device, data can be seen relating to doses that have already been administered or doses contained in the injection device which may be administered or pertaining to the current dispensing operation. However, problems can arise if this display is not functioning correctly due to an error, for example due to a user mistakenly assuming that the injection device still contains a bigger quantity of substance than it actually does.

Accordingly, embodiments provide a display on an injection device, which permits a reliable display of a quantity of substance or dose.

A display element for displaying administering parameters, such as a quantity of a substance still contained in an injection device or already dispensed from an injection device, for example from an ampoule inserted in the injection device, may be coupled, e.g., directly coupled with, a dispensing element of the injection device, such as a plunger rod or threaded rod that causes a forward movement of a stopper in an ampoule or in a reservoir. Coupling the display element with the forward feed element, for example in a direct connection, may rule out errors in the display because no or only a few intermediate elements may cause errors or be susceptible to errors. Accordingly, a robust and reliable direct display is achieved, which may be used as a display of the remaining quantity or a real-time display. In terms of administering parameters, the display element may additionally display the time of dispensing or dispensing time to enable a user to check the dispensing time or record the dispensing time so that it can be used for evaluation purposes.

The display element may be connected directly to the dispensing element, e.g., mounted so that it is prevented from moving or rotating relative to it, and may include a marking on an external face in the circumferential direction and/or longitudinal direction, for example, serving as a dose display, which may be read through a window or by means of a marking past which the display element is moved by a rotating and translating movement.

Alternatively, the display element may be coupled with the forward feed or dispensing element, e.g., not directly connected to the latter, in which case the coupling may be established by means of a thread engagement or another movement or a mechanism transmitting force, such as a screw, a cog or a gear mechanism. For example, the display element may have a thread and, if the display element is provided in the form of a sleeve, an internal thread, which locates in an external thread of a plunger rod or threaded rod so that the display element, which is mounted in the injection device so that it is not axially movable but is rotatable, is rotated by a rotating or translating movement of the threaded rod or plunger rod, and a reading can be taken as a result of the rotation, e.g., from print on the external face of the display element alongside a non-rotatable scale to indicate the dose that has been dispensed or is still available. In the case of a threaded engagement, the thread may be one that is not retained by friction, thereby permitting easy rotation of the display element such that the display element may not cause an obstruction to a priming or dispensing movement.

A display element may be provided on an ampoule introduced into the injection device, as opposed to on an injection device. The ampoule may be coupled with a coupling element of the injection device so that a movement of a stopper of the ampoule, for example, is not converted into a co-operating movement of the display element until the ampoule is introduced into or after it has been introduced into the injection device, thereby resulting in a real-time display.

According to further embodiments, an injection device with a display element of the type described above is provided.

The injection device including at least one orifice, such as a viewing window for example, enables a reading to be taken from a marking of the display applied to the external face of the display element provided in the injection device.

To mount the display element so that it is not axially movable but is rotatable, an annular groove or an annular web may be provided on the injection device for example, in which a co-operating mating element locates, e.g., an annular web or an annular groove of the display element.

The injection device may be configured so that the display element is slideable inside the injection device, e.g., when an ampoule is introduced, and the display of the display element may not be read from a window if no ampoule has been introduced. for example, a color code on the circumferential face of the display element may indicate that no ampoule has been introduced. The display element may not be pushed relative to a reading position, such as a viewing window for example, to enable the display or print of the display element to be seen until the ampoule has been inserted, for example by the ampoule introduction operation. This being the case, the display element may be disposed either completely or partially inside the ampoule.

In another aspect, a locking mechanism, such as a setting mechanism or a setting element of an injection device, may be provided to prevent the injection device from being operated. For example, locking the setting element to prevent it from rotating, and the locking action preventing operation or rotation, may be released by pushing an ampoule into the injection device.

When using an injection device into which an ampoule is inserted prior to use, for example, a 2-chamber ampoule which is inserted and mixed immediately prior to use, problems may arise if a user of the injection device performs a setting or operating procedure prior to introducing the ampoule. Accordingly, a mechanical lock and an injection device with such a mechanical lock may be provided to increase reliability during the operating sequence of an injection device in which an ampoule is to be inserted.

According to such embodiments, wherein the embodiment includes a housing, an operating element, e.g., dose setting knob, push-button or rotating knob, mounted in the housing or connected to or coupled with the housing may be mounted in the housing or coupled with or connected to the housing so that the operating element may be retained by a first retaining connection in a first position relative to the housing of the injection device. That is, the operating element may be prevented from moving axially. The retaining connection may be designed so that it is released during and after introducing or inserting or pushing in an ampoule, so that the operating element is pushed into a second retaining position offset from the first retaining position, e.g., axially in the proximal direction, after the ampoule has been introduced, where it is retained by a second retaining connection. In this respect, the operating element may be moved relative to the housing of the injection device due to the introduction or insertion of the ampoule. For example, the operating element may be pushed in the proximal direction out of the injection device. However, the injection device may also be configured so that a coupling or a coupling element is movable in response to introducing the ampoule such that it is moved into contact with a proximal ampoule edge, for example, and thus releases the operating element. The operating element may be stationary or may be movable relative to the injection device.

The operating element or coupling element may be mounted in the injection device such that it is not moved out of the first retaining connection into the second retaining connection until an ampoule has been fully introduced or pushed in or screwed in, which may take place at the same time as two substances contained in the ampoule are being mixed. For example, the operating or coupling element may be disposed in the injection device so that an ampoule to be introduced or pushed in, which is of a known size or dimension, does not move into contact with the coupling or operating element until the last part of the insertion distance so that the ampoule may be screwed or mounted into the injection device prior to this final distance without making contact with or moving the coupling or operating element. Upon the ampoule subsequently making contact with the coupling or operating element and causing movement due to the fully inserted ampoule, that the coupling element unlocks the mechanism for operating the injection device or the operating element is released for use and for setting by a user, e.g., by moving out of the housing of the injection device.

The first and/or second retaining connection may be provided in the form of a catch connection, for example, in which case a catch ring may project radially inwardly or radially outwardly from a coupling or operating element and establish a first retaining connection with an annular groove of the injection device or the housing, and another annular groove of the injection device or the housing establishes the second catch connection. Likewise, the retaining element may also be provided in the form of other mechanical couplings, which may be released when a specific minimum force is acting on this coupling.

According to certain embodiments, the mechanical lock may be established by preventing the setting element from rotating, e.g., by guiding extending grooves of the setting element so that the setting element is prevented from rotating in a distal position. After screwing in an ampoule, the setting element, locked to prevent rotation, is pushed in the proximal direction such that the grooves serving as the anti-rotation lock are pushed out of the elements retaining and guiding these grooves, for example of the injection device or housing, thereby permitting a rotation and hence operation of the setting element. Likewise, a coupling element may be provided, which does not release a rotating movement of the setting element until after a movement in the proximal direction. For example, this coupling element may be of an annular design and may have inwardly and outwardly pointing webs which locate in grooves of the setting element and grooves of the injection device or housing and thus prevent a rotation of the setting element relative to the housing of the injection device. If the setting element is moved by means of an ampoule introduced into the injection device and screwed in, for example against the force of a spring biasing the coupling element in the distal direction until the webs of the coupling element are pushed out of the grooves of the setting element and/or out of the grooves of the injection device, the coupling between the setting device and injection device is released and the injection device may be operated once the ampoule has been pushed, e.g., fully pushed, into the injection device.

When injection devices such as injection devices for dispensing a measured quantity of substance are manufactured, dose setting mechanisms may be configured for a specific application. For example, to dispense a large quantity of substance or to prepare a long stroke of the setting element, an internal thread of the injection device in which a threaded rod or a setting element is designed to be guided is provided with a large pitch. If an existing injection device must also be used to dispense a substance which requires measurement in smaller doses, for example, a new, compatible injection device is required to provide an internal thread with a smaller pitch, for example.

Accordingly, embodiments provide an injection device which can be used substantially universally.

An injection device, according to certain embodiments, includes an internal thread for guiding a threaded rod or setting element. The internal thread is configured such that it has several contact faces to enable different threaded rods with an external thread of differing pitch to be guided without having to change or replace the internal thread of the injection device. In such an embodiment, the internal thread may be configured with individual thread portions. The thread portions offset from one another in the circumferential direction, which may extend across 1/N-th of the circumference, N being a natural number. For example, the thread portions are configured to extend across a half, a third or a quarter circumference on the internal face of the injection device or a housing thereof. Individual thread portions generally have at least two contact faces on which threads of differing pitch can be guided.

The thread portions may have at least four side faces in which a thread can be guided, and two respective side faces are disposed in parallel. Contact faces for guiding the different threads alternate indirectly or directly in the circumferential direction. In other words, for a movement around a thread segment or thread part-element, the contact faces may adjoin one another directly or may be used by thread-portion segments or thread-portion lengths, which may be used to guide other threads of differing pitch.

It may be possible for such a thread or thread-part length to be configured so that more than two threads of differing pitch can be guided. To this end, the thread or the thread segment contact faces may have a minimum pitch and a maximum pitch pre-defined by the threads segments for guiding threaded rods with a variable pitch. Another option is for the thread segments to have several contact faces and be disposed in the circumferential direction, such that threads of defined pitches, such as three different pre-defined pitches, can be guided, for example.

Depending on the configuration of a thread segment and/or contact faces of the thread segment, and depending on the distribution of the thread segments in the circumferential direction, it may be possible to define which external thread can be guided by such a thread segment or several such thread segments constituting an internal thread of differing pitch.

Accordingly, elements with an external thread of differing pitch may be guided in a single injection device or in a single internal thread without the internal thread or the injection device having to be structurally modified. Accordingly, the same injection device may be used for different applications in which short or long strokes are needed in order to set doses.

When a substance contained in an ampoule in an injection device has been fully or partially dispensed (e.g., when the substance is forced by stopper inside the ampoule via a threaded or plunger rod acting on the stopper), it may be that this plunger rod or threaded rod is inadvertently pulled back inside the injection device, which can lead to incorrect operation of the injection device.

According to certain embodiments, a threaded rod and an injection device with such a threaded rod is provided that prevents the threaded rods from being pulled out once it has been pushed in.

A threaded rod, thus includes an anti-rotation locking element, such as a claw lock disposed on the threaded rod. In some implementations, the claw lock is provided on the proximal end of the rod so that the anti-rotation lock or claws can be inserted into mating elements which retain or locate these anti-rotation locking elements or claws when the threaded or plunger rod has been moved to a pre-defined end (e.g., distal end) position inside the injection device. Accordingly, the claws or anti-rotation locking elements in which the claws or anti-rotation locking elements of the threaded rod locate may be fixedly connected to the injection device or a part thereof, such as an injection device housing. A threaded rod pushed into the injection device may therefore no longer be rotated once the claws or anti-rotation locking elements have been pushed into the co-operating anti-rotation locking elements of the injection device because the locating action of the elements, such as the locating action of projecting webs in grooves, couple the threaded or plunger rod with the injection device to prevent rotation, which prevents turning movement. A threaded rod may therefore be retrained in an inserted end position because rotation is no longer possible due to the claw lock and an axial movement is prevented by the thread coupling.

Consequently, embodiments of the threaded rod serve as a means of retaining and securing the threaded rod in the end position so that no other retaining mechanism is needed in the injection device. That is, threaded rod is already secured by the claw lock provided or disposed on it.

The anti-rotation locking elements of the injection device may be provided in the form of indentations in or claws on the injection device or parts of the injection device, such as the rotating sleeve. A variety of mating element configurations may be implemented for the injection device, and anti-rotation locking elements may be configured so that they establish a positive connection with the anti-rotation locking elements of the threaded rod locating in or pushed into the anti-rotation lock mating elements such that any rotation of the threaded rod in the proximal and/or distal direction is prevented by the positive connection. The anti-rotation locking elements on the threaded rod may be resiliently mounted, for example, providing for a snap or latch into the anti-rotation lock mating elements of the injection device in the distal end position. The anti-rotation locking elements of the threaded rod may also be fixedly mounted, and at least readily or partially deformable so that they are able to snap or latch into the anti-rotation lock mating elements of the injection device in the distal end position. Once the anti-rotation locking elements have snapped or latched into the anti-rotation lock mating elements, a positive connection to the anti-rotation lock mating elements is formed so that a movement or rotation of the threaded rod in the proximal and/or distal direction can be prevented.

BRIEF DESCRIPTION OF THE DRAWINGS

FIG. 3A is a diagram in section illustrating an alternative view along line A-A indicated in FIG. 1;

FIGS. 3B-D are cross-sections B-B and C-C of the diagrammatic cross-section and a detail D in the alternative view of FIG. 1;

FIG. 4A shows the injection device illustrated in FIG. 3 after mixing and with the mechanism extracted;

FIGS. 4B-D are cross-sections B-B and C-C of the diagrammatic cross-section and a detail D of the alternative embodiment of FIG. 3;

FIG. 5A shows the injection device illustrated in FIG. 4 after setting the dose and tensing the spring;

FIGS. 5B-E are cross-sections B-B, C-C and E-E of the diagrammatic cross-section and a detail D of the alternative embodiment of FIG. 4;

FIG. 6A shows the injection device illustrated in FIG. 5 after dispensing the dose with the mechanism blocked and the spring relaxed;

FIGS. 6B-C are cross-sections B-B and C-C of the diagrammatic cross-section of the embodiment of FIG. 5;

FIG. 10A is a perspective view of one embodiments of the dose setting mechanism of the injection device;

FIG. 10B shows the dose setting mechanism from FIG. 10A with a view of the proximal part in cross-section;

FIGS. 11A-11C illustrate different embodiments of a real-time or remaining quantity display;

FIGS. 12A-12B illustrate an embodiment of a claw lock in accordance with the present invention.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc. Generally, unless otherwise indicated, relative positional or orientational terms (e.g., upwardly, downwardly, above, below, etc.) are intended to be descriptive, not limiting.

Figure 1:
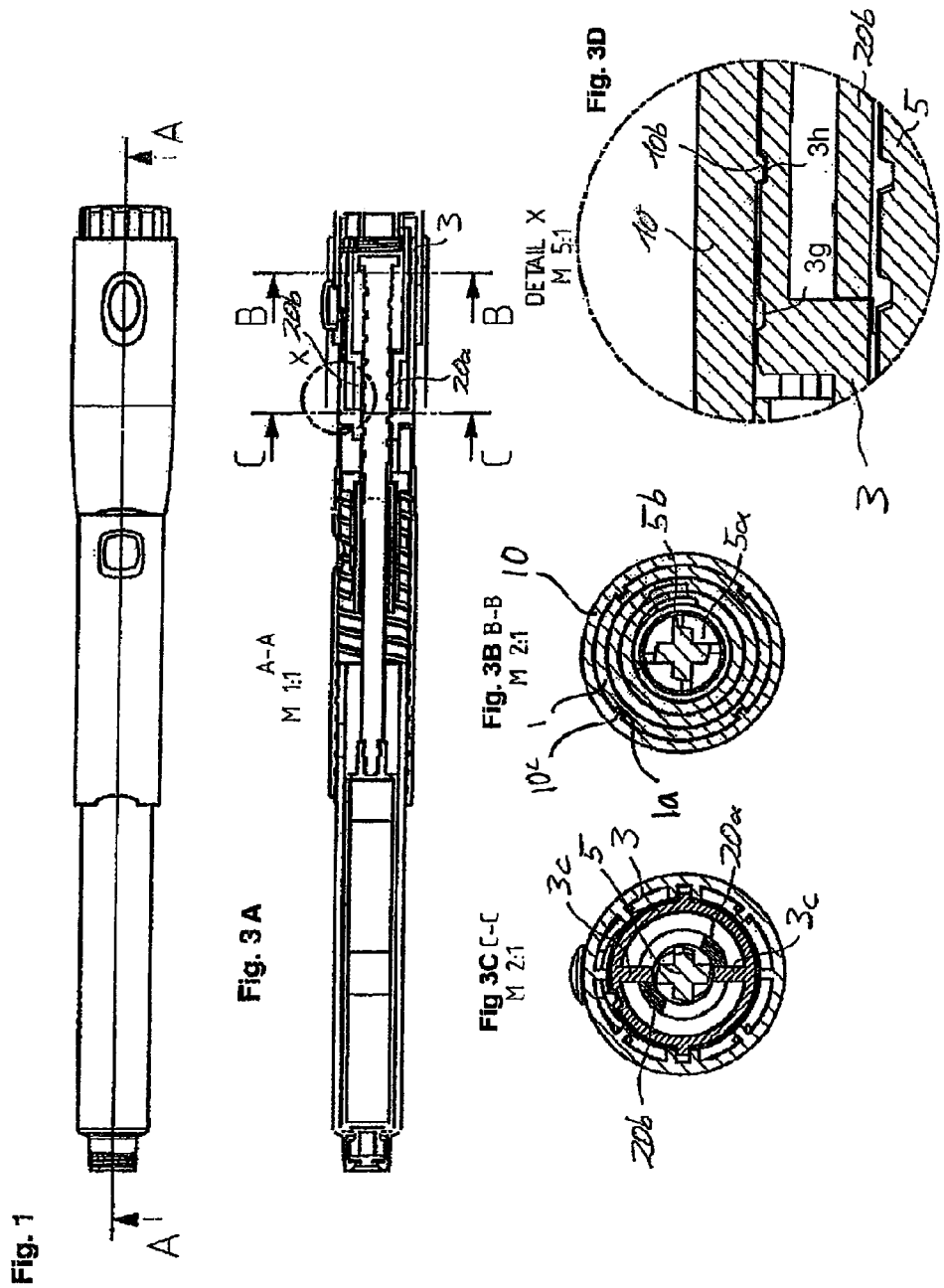
FIG. 1 is a plan view showing an embodiment of an injection device in accordance with the present invention.

FIG. 1 illustrates a fixed-dose pen whereby the dose to be dispensed can be set by the dose setting knob 1.

The pen has a threaded rod 5, which, as illustrated in the sections of FIGS. 3A to 6C, has four tines 5b constituting the shape of a star in cross-section, thereby enabling a robust and simple setting of the fixed dose.

The threaded rod 5 may be configured with a star-shaped cross-section (in the shape of a Swiss cross) but may have more or fewer tines 5b than the Swiss cross.

Figure 2:
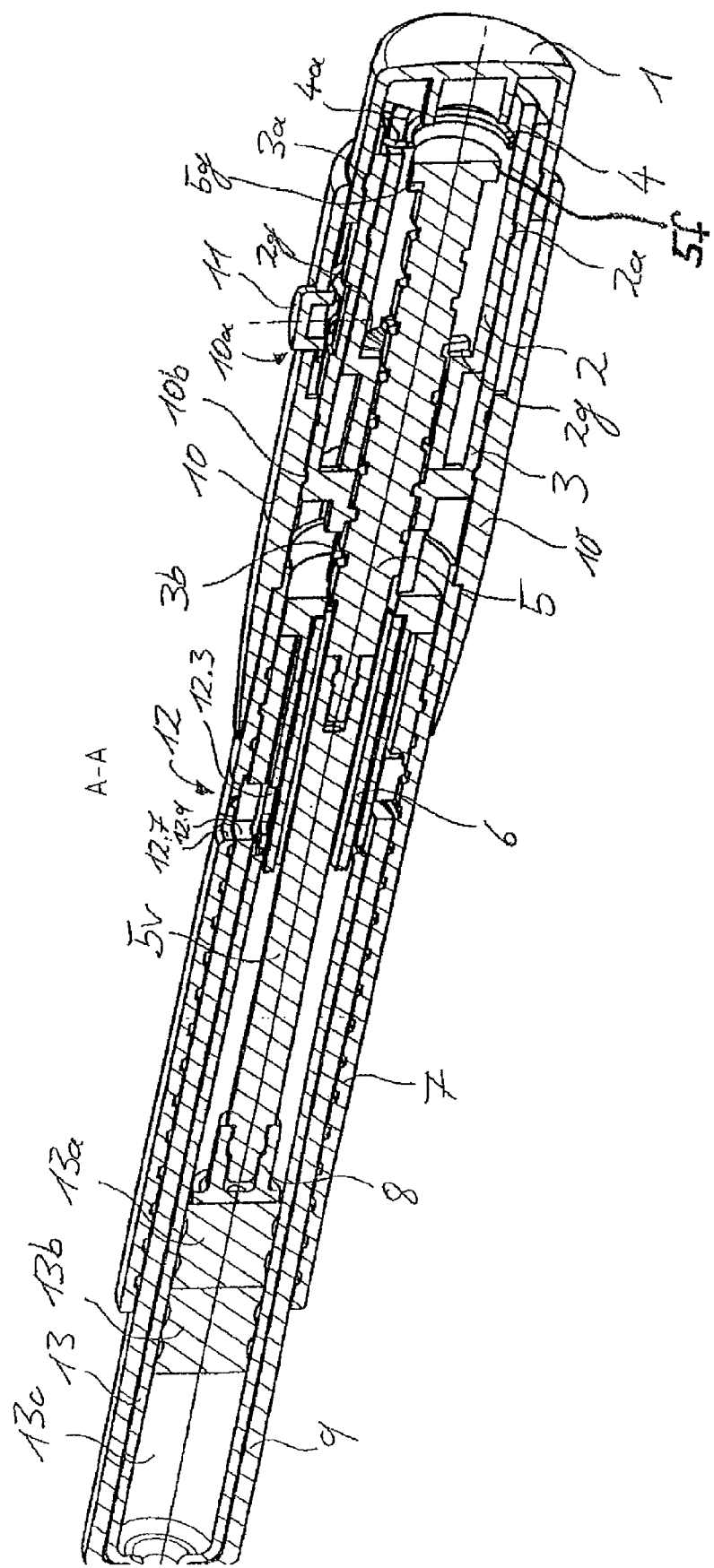
FIG. 2 is a perspective view of the injection device in cross-section along line A-A indicated in FIG. 1.
Figure 8:
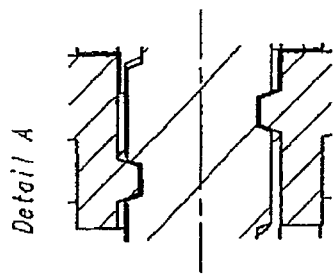
FIG. 8 shows detail A from FIG. 7 with a view to illustrating the thread engagement of the guide sleeve in the threaded rod.

FIG. 2 shows a perspective view of the pen from FIG. 1 in section along A-A.

The guide sleeve 3 may be connected to the housing 10 and is mounted so that it is not able to rotate relative to the housing 10. The rotating sleeve 2 is mounted inside the guide sleeve 3 by means of a snapper bead 2a so that it can rotate but can not move axially. Mounted on the external face of the guide sleeve 3, also by means of a snapper bead 3a, is the dose setting knob 1, which is able to rotate but can not move axially. Disposed on the proximal end of the rotating sleeve 2 and connected to the guide sleeve 3 and the rotating sleeve 2 is a spring element 4, which is provided in the form of a spring wire or spring strip wound, for example, two to three times, so that when the rotating sleeve 2 is rotated relative to the guide sleeve 3, the spring 4, which is connected at one time to the guide sleeve 3 and at one time to the rotating sleeve 2 due to bends 4a at the opposite ends, is tensed and thus affords a rebound force opposing the setting rotation movement.

The dose setting knob 1 is configured such that it is not pulled out axially but is rotatable. Disposed on the internal face of the dose setting knob 1 are four webs pointing in the axial direction which locate in co-operating grooves of the rotating sleeve 2 and thus couple the dose setting knob 1 with the rotating sleeve 2 so that a rotating movement of the dose setting knob 1 can be transmitted to produce a rotating movement of the rotating sleeve 2. The rotating knob 1 and rotating sleeve 2 may also be configured integrally or a single element.

The rotating sleeve 2 includes snapper elements 2b biased radially inwardly and in the embodiment illustrated as an example in section C-C in FIG. 5C has two oppositely lying snapper elements 2b biased radially inwardly. These snapper elements 2b locate in the four grooves 5a of the threaded rod 5 during the priming movement or are rotated past the tines 5b. During the priming operation, the threaded rod 5 is mounted so that it can not rotate because it is retained by a snapper element 3b of the guide sleeve 3. The rotating sleeve 2 has a snapper element 2c biased radially outwardly, which is rotated into a window or orifice 3c of the guide sleeve 3 when the priming operation has ended, as illustrated in section B-B and detail D in FIGS. 5B and D, and latches in this window 3c so that the rotating sleeve 2 can no longer be pushed back relative to and inside the guide sleeve 3 due to the force of the spring 4 biased due to the setting operation. When the trigger button 11 of the pen lying above the window 3c of the guide sleeve 3 is depressed the snapper element 2c of the rotating sleeve 2 biased radially inwardly is pushed out of the window 3c of the guide sleeve 3, thereby releasing the rotating sleeve 2 from the guide sleeve 3 so that it can be rotated back by the setting distance due to the force of the biased torsion spring 4.

Provided on the distal end of the rotating sleeve 2 are two oppositely lying stops, webs or cams 20a, 20b projecting in the axial direction, which permit a maximum rotation of the rotating sleeve 2 of approximately 110° because these cams move into contact with cams 3c of the guide sleeve 3, likewise in the radial direction but directed in the proximal direction.

When turned back in the dispensing direction indicated by arrow A in section C-C of FIG. 5C, the cams 2b of the rotating sleeve 2 biased radially inwardly latch into the grooves 5a of the threaded rod 5 extending in the axial direction so that the threaded rod 5 is also driven along by the backward rotating movement of the rotating sleeve 2 and is thus guided in the distal direction by an internal thread 3d of the guide sleeve 3 and screwed into the pen. This causes the stopper 13a, 13b of the ampoule 13 to be moved into the ampoule 13 by the ram 8 provided on the distal end of the threaded rod 5 or an extension element 5v connected to it, thereby dispensing thee substance 13c contained in the ampoule 13.

When dispensing is complete, the pen can be primed again by rotating the dose setting knob 1 and the same dose can then be dispensed.

The threaded rod 5 may be fabricated by an injection casting process using two mould halves if the threaded rod 5 has the cross-section of a simple cross. In the axial direction of the threaded rod 5, the grooves 5a in which the snapper 2b of the guide sleeve 2 biased radially inwardly locates may be of a continuous design and thus interrupt the thread 5c on the external face of the threaded rod 5. This enables high or steep faces to be produced for the snapper 2b.

The outer or peripheral regions of the threaded rod 5 may have an incline 5d so that the snapper 2b of the rotating sleeve 2 biased radially inwardly is able to slide more easily over it during priming. This results in a higher face 5e on the side of the groove 5a of the threaded rod 5 extending in the axial direction, in which the snapper 2b of the rotating sleeve 2 biased radially inwardly locates, thereby reliably preventing the rotating sleeve 2 from turning back relative to the threaded rod 5.

Figure 9:
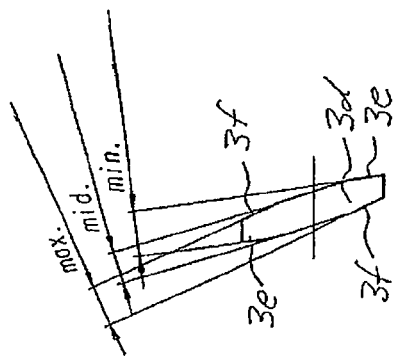
FIG. 9 shows the thread design of the guide sleeve illustrated in FIG. 8 with different contact faces for guiding different threaded rods with an external thread of differing pitch.
Figure 7:
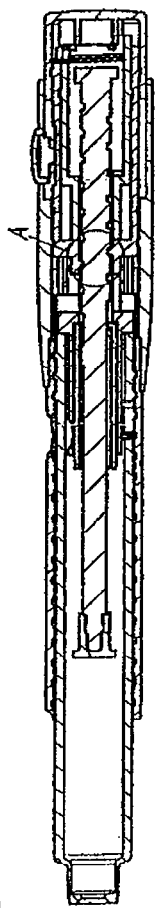
FIG. 7 is a view in cross-section showing an injection device without an ampoule inserted.

According to such embodiments, the pitch of the threaded rod 5 may be easily changed during the manufacturing process so that different dose quantities to be dispensed can be achieved depending on the respective thread pitch which specifically exists for a same setting rotating movement of 110° for example. One option may be to change the internal thread 3d of the guide sleeve 3 corresponding to the altered pitch of the external thread 5c of the threaded rod 5. Alternatively, the internal thread 3d of the guide sleeve 3 may be configured so that different pitches of the external thread 5c of the threaded rod 5 may be guided within a region of a minimum pitch pre-defined by the internal thread 3d to a maximum pitch pre-defined by the internal thread 3d. FIG. 9 illustrates a single thread turn of the internal thread 3d of the guide sleeve 3 opened out so as to be viewed flat with a minimum and a maximum pitch resulting from contact edges 3e and 3f of the internal thread 3d.

A claw lock may be provided on the threaded rod 5 to prevent the injection pen from further priming once the last dose has been dispensed. At the proximal end of the threaded rod 5, a wider region 5f is provided from which four distally pointing webs 5g project in the axial direction, which move into co-operating mating stops 2g of the rotating sleeve 2 or are pushed into them once the last dose has been dispensed. As this happens, the threaded rod 5 is moved axially into the rotating sleeve 2 to the degree that the claws or webs 5g of the threaded rod 5 lie against the co-operating mating stops 2g of the rotating sleeve 2. The webs of the claw lock may move into the co-operating mating stops 2g due to a slight or partial mechanically deformation or compression when the injection device is operated and relax and move into the mating stops provided in the form of recesses, indentation, notches, grooves, claws or snap lock portions, for example, upon reaching the end position. When the injection device is operated, the resiliently mounted claws 5g slide along the mating stop 2g as illustrated in FIG. 12A, being deflected in the direction indicated by the arrow. Once the dose has been dispensed, the claws 5g snap into the mating stop 2g as illustrated in FIG. 12B to prevent further injection device priming. Irrespective of the design of the claw lock 5g and the mating stops 2g, when the last dose has been dispensed, the pen may not be primed because the threaded rod is held so that it can not be rotated by the positive connection between the claw lock 5g and mating stops 2g. The threaded rod 5 is mounted so that it can not rotate in the guide sleeve 3 and the dose setting knob 1 and rotating sleeve 2 are prevented from rotating due to the claw coupling 2g, 5g preventing additional priming.

A two-chamber ampoule 13 may be introduced into or screwed into the injection device. For mixing purposes, the ampoule 13 is screwed into the pen and, once the ampoule 13 has been screwed sufficiently far into the pen it makes contact with the guide sleeve 3 and pushes it together with the dose setting knob 1 in the proximal direction of the pen. As a result, the dose setting knob 1 is pushed out of the pen to allow pen priming.

For example, as illustrated in FIGS. 2-4, in one embodiment, the dose setting knob 1 may be mounted in the housing 10 or connected to or coupled with the housing 10 so that the dose setting knob 1 may be retained, directly or via an intermediate member such as the guide sleeve 3, by a first retaining connection in a first position relative to the housing 10 of the injection device (FIG. 3). That is, in the first retaining connection, the dose setting knob 1 may be prevented from moving axially. The retaining connection may be configured such that it is released during introduction of the ampoule 13, so that the so that the dose setting knob 1 is pushed into a second retaining position (FIG. 4) axially offset from the first retaining position, e.g., axially in the proximal direction, after the ampoule 13 has been introduced, where it is retained by a second retaining connection. In this respect, the dose setting knob 1 may be moved relative to the housing 10 of the injection device due to the introduction or insertion of the ampoule 13. For example, the dose setting knob 1 may be pushed in the proximal direction out of the injection device.

The dose setting knob 1 may be mounted in the injection device such that it is not moved out of the first retaining connection into the second retaining connection until the ampoule 13 has been fully introduced or pushed in or screwed in, which may take place as two substances contained in the ampoule 13 are being mixed. For example, the dose setting knob 1 may be disposed in the injection device so that an ampoule 13 to be introduced or pushed in, which is of a known size or dimension, does not act upon the dose setting knob 1, either directly or indirectly via an intermediate member such as the guide sleeve 3, until the last part of the insertion distance so that the ampoule 13 may be screwed or mounted into the injection device prior to this final distance without acting upon the dose setting knob 1. Upon the ampoule 13 subsequently acting upon the dose setting knob 1, and causing movement due to the fully inserted ampoule, the dose setting knob 1 is released for use and for setting by a user, e.g., by moving out of the housing 10 of the injection device.

The first and/or second retaining connection may be provided in the form of a catch connection, for example, in which one or more first catch elements, such as grooves or protrusions may project radially inwardly or radially outwardly from the dose setting knob 1 or an intermediate member coupled to the dose setting knob 1, such as the guide sleeve 3, and establish a retaining connection with one or more second catch elements, such as complementary grooves or protrusions of the injection device or the housing 10. For example, as shown in FIGS. 3D and 4D, a first groove 3g formed on an outer surface of the guide sleeve may form a first retaining connection with a protrusion 10b formed in an inner face of the housing 10, and a second groove 3h formed in an outer surface of the guide sleeve 3, axially offset relative to the first groove 3g, may form a second retaining connection with the protrusion 10b.

According to certain embodiments, the mechanical lock may be established by preventing the dose setting knob 1 from rotating, e.g., by guiding extending grooves 1a of the dose setting knob 1 so that the dose setting knob 1 is prevented from rotating in a distal position (FIG. 3). After screwing in an ampoule, the dose setting knob 1, locked to prevent rotation, is pushed in the proximal direction (FIG. 4) such that the grooves 1a serving as the anti-rotation lock are pushed out of the elements retaining and guiding these grooves, for example retaining elements 10c of housing 10, thereby permitting a rotation and hence operation of the dose setting knob 1.

Figure 13A:
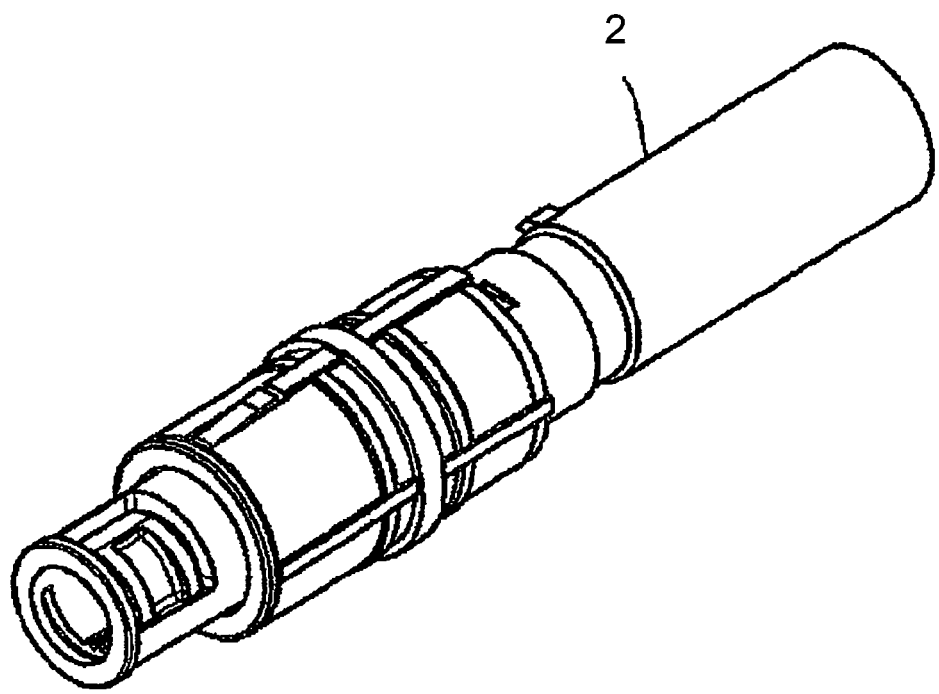
FIGS. 13A-13G illustrate an embodiment of a mechanical lock in accordance with the present invention.
Figure 13B:
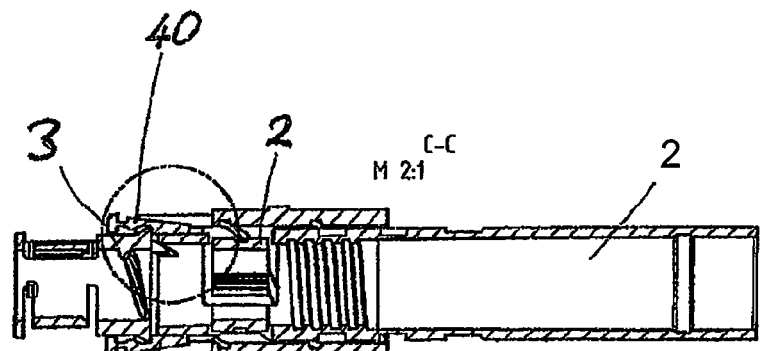
Figure 13C:
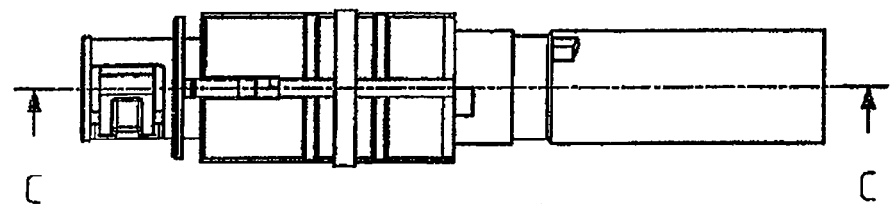
Figure 13D:
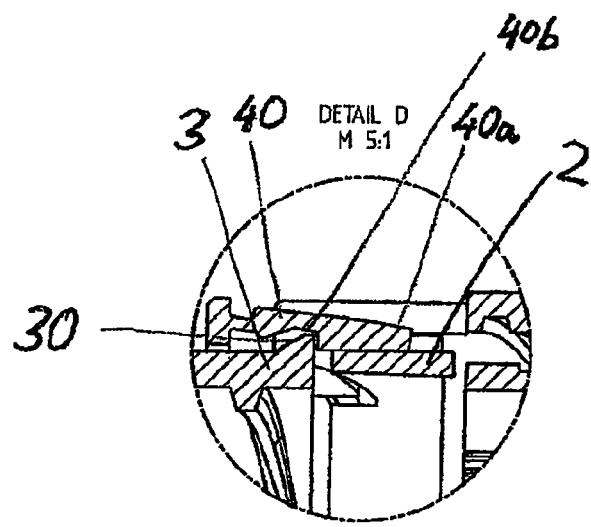

In some embodiments, the injection device may also be configured so that a coupling or a coupling element is movable in response to introducing the ampoule 13 such that it is moved into contact with a proximal ampoule edge, for example, and thus releases an operating element, such as the dose setting knob 1 and/or the rotating sleeve 2. For example, as illustrated in FIGS. 13B and 13C, and the detailed view of FIG. 13D, a catch ring 40 or locking ring is provided, the fork-shaped locking pawls 40a of which extend into co-operating recesses of the rotating sleeve 2 and prevent the rotating sleeve 2 from rotating. Since the injection device is primed by rotating the rotating sleeve 2, the injection device is prevented from being primed or charged by the catch ring 40 locating in the rotating sleeve 2.

In order to unlock the catch ring 40 and the rotating sleeve 2, the ampoule sleeve, which was screwed into the pen in order to mix the two-chamber ampoule is screwed in.

Figure 13E:
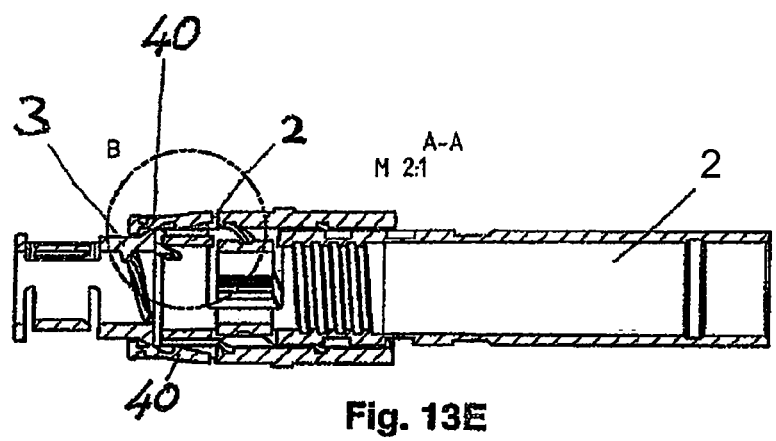
Figure 13F:
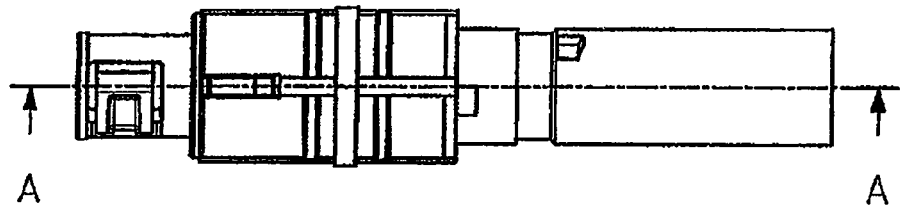
Figure 13G:
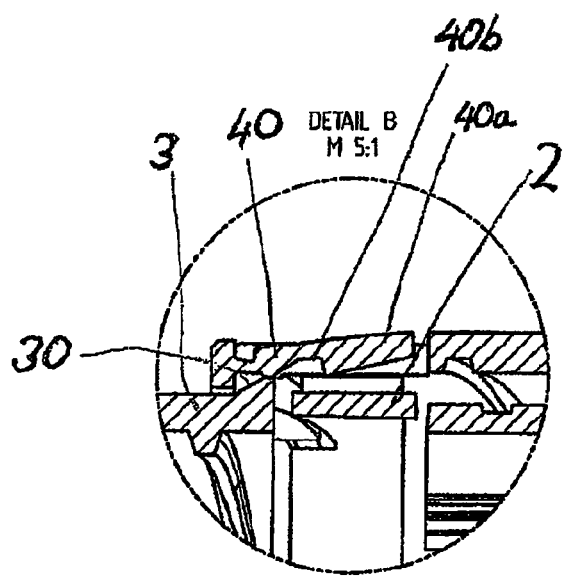

Over the final portion of the screwing-in operation (e.g., such as the last 1 to 3 mm, for example the last approximately 2 millimeters), the catch ring 40 is moved through the ampoule sleeve from the locked position into an unlocked position in which the catch ring 40 is no longer latched to the rotating sleeve 2. Once the ampoule 13 has been sufficiently screwed in, the two locking pawls 40a of the catch or locking ring 40 are pushed out, as illustrated in FIGS. 13E to 13G, by means of inclined surfaces 40b or sliding surfaces on the internal faces of the two fork-shaped locking pawls 40a and slide relative to and along inclined surfaces 30 or sliding surfaces provided on the guide sleeve 3 so that the catch ring 40 moves out of engagement with the rotating sleeve 2 and the rotating sleeve 2 is released so that it can effect rotating movements, for example for setting and metering doses.

In addition, a display sleeve 6 is also provided on the threaded rod 5, which is fixedly connected to the threaded rod 5, i.e. so that it can not rotate and can not move axially. The dose quantities still to be dispensed are displayed on the external face of the display sleeve 6 in the circumferential direction. A viewing window 12 (FIG. 2) may be made from transparent materials or provided in the form of orifices 12.3, 12.9, 12.7 in the guide sleeve 3, ampoule holder 9 and threaded sleeve 7 (from the inside out).

The display sleeve 6 is pushed into the ampoule 13 as the latter is being mixed (not before). In principle, the display sleeve 6 could also be mounted on the rear stopper 13a so as to be rotatable, in which case the display sleeve 6 is firstly uncoupled from the mechanism of the pen and disposed in the ampoule part.

Since there is a direct coupling between the display sleeve 6 and the threaded rod 5, the display sleeve 6 is not able to slip. This also prevents an incorrect display, even if the pen has been subjected to a strong impact because it has been dropped.

The guide sleeve 3 also serves as a view guard because the window 12.3 in the guide sleeve 3 is moved in the threaded sleeve 7 relative to the window 12.7 before the ampoule 13 is screwed in. It is not until the ampoule 13 has been screwed in and mixed that the window 12.3 of the guide sleeve 3 moves into alignment with the window 12.7 of the threaded sleeve 7 so that the display sleeve 6 mounted on the threaded rod 5 can be seen and read.

The trigger button 11 is positioned by means of an orifice 10a in the housing 10 and has two resilient arms 11a in the circumferential direction which push the trigger button 11 radially outwardly away from the guide sleeve 3. The resilient arms 11a describe a radius which is smaller than the external radius of the guide sleeve 3, thereby permitting the biasing action of the trigger button 11 directed radially outwardly.

The display 6 is directly coupled with the plunger rod or threaded rod 5 in the embodiments illustrated in FIGS. 11A and 11B and can be rotated without any frictional resistance. The display element 6 in the pen is secured so that is prevented from moving axially.

The plunger rod 5 has a thread or thread part-piece on the external face in which the display 6 or, if the display is moved in axial translation, a transmission element coupled with the display 6, for example a gear or a gear with an internal thread as illustrated in FIG. 11C, can locate. If opting for a translating movement, a gap is formed between the gear directly coupled with the toothed rack and the display, through which the guide sleeve 3 can be passed for example.

If, instead of the toothed rack, a rotating mechanism is used in conjunction with a plunger rod, the remaining quantity display can also be used. To this end, the remaining quantity display element 6 could be mounted on the plunger rod 5 so that it is prevented from rotating for example, so that the plunger rod 5, which is itself mounted in the pen so that it is prevented from moving axially, moves through the remaining quantity display 6 during dispensing A remaining quantity display 6 that is not retained by friction can be achieved by means of an appropriate thread pitch which will depend on the material and is approximately 45° in the embodiment described as an example.

The coupling between the remaining quantity display element 6 and toothed rack is configured such that when the toothed rack 5 is moved fully in, the remaining quantity display element has effected a full rotation of 360°.

In the case of a rotation of >360°, the display element 6 may be designed so that it can also be moved by means of an external thread.

It would also be conceivable to use an axially displaceable remaining quantity display 6, which moves in the axial direction of the pen as the toothed rack 5 moves, for example by means of a thread engagement on the external face of the remaining quantity display 6 in an internal thread in the housing of the pen. For example, a pen with a pre-set constant dose may be used, in which case the remaining quantity display will display 14 maximum possible units which can be dispensed for example, which can be counted back to 0 starting from an initial state.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device comprising a housing and a rotatable operating element, wherein the operating element is mounted in the housing such that it is retained in a first position by a first retaining connection that prevents the operating element from rotating in a dose setting operation when an ampoule has not been introduced into the injection device, and introduction of the ampoule into the injection device causes the operating element to move into a second position axially offset from the first position where it is retained by a second retaining connection and may be rotated in the dose setting operation, wherein the operating element comprises an anti-rotation lock, said lock being locked in the first position in which the first retaining connection is active.

2. The injection device of claim 1, wherein the operating element comprises a rotating dose setting knob mounted in the injection device configured to be pushed out of the housing of the injection device when the ampoule has been pushed in.

3. The injection device of claim 1, wherein the first retaining connection or the second retaining connection are releasable connections upon the action of a pre-defined force.

4. The injection device of claim 1, wherein the operating element or an intermediate element coupled to the operating element such that is axially fixed relative to the operating element comprises one or more first catch elements, wherein the housing comprises one or more second catch elements, and wherein the first catch elements cooperate with the second catch elements to form the first and second retaining connections.

5. The injection device of claim 4, wherein the first catch elements are formed on an outer surface of the intermediate element and the second catch elements are formed on an inner surface of the housing.

6. The injection device of claim 4, wherein the operating element further comprises one or more first blocking elements and the housing further comprises one or more second blocking elements, and wherein the first and second blocking elements cooperate to block rotational movement of the operating element when the operating element is in the first position.

7. The injection device of claim 1, further comprising a piston rod configured to be driven in an advancing direction to deliver a substance contained in the ampoule, wherein the operating element is mounted in the housing such that an insertion movement of the ampoule counter to the advancing direction causes the operating element to move into the second position.

8. The injection device according to claim 1, wherein the first and second retaining connections comprise a catch ring projecting from a coupling or the operating element and engageable respectively with a first and a second annular groove of the injection device or the housing.

* * * * *

UNITED STATES PATENT AND TRADEMARK OFFICE
CERTIFICATE OF CORRECTION

PATENT NO. : 8,679,071 B2  
APPLICATION NO. : 12/371350  
DATED : March 25, 2014  
INVENTOR(S) : Hirschel et al.

Page 1 of 1

It is certified that error appears in the above-identified patent and that said Letters Patent is hereby corrected as shown below:

IN THE SPECIFICATION

| Column | Line | | Should Read |
|---|---|---|---|
| 10 | 33 | the guide sleeve 3 is depressed the snapper element | the guide sleeve 3 is depressed, the snapper element |
| 14 | 25 | and toothed rack is configured such that | and toothed rack 5 is configured such that |

Signed and Sealed this  
First Day of July, 2014

Michelle K. Lee  
*Deputy Director of the United States Patent and Trademark Office*